United States Patent [19]

Inouye

[11] Patent Number: 4,657,720
[45] Date of Patent: Apr. 14, 1987

[54] METHOD AND APPARATUS FOR LOCATING AND EMBEDDING A SPECIMEN

[76] Inventor: Tohru Inouye, 175 E. Delaware Pl., Chicago, Ill. 60611

[21] Appl. No.: 729,949

[22] Filed: May 2, 1985

[51] Int. Cl.⁴ .................. A01N 1/00; B29C 39/02; B29C 39/36; B32B 31/00
[52] U.S. Cl. .................... 264/275; 264/139; 264/158; 264/261; 264/279; 264/279.1; 269/7; 425/110; 425/125; 425/171; 425/173; 425/444; 427/4
[58] Field of Search .......... 264/40.2, 135, 139, 264/158, 334, 279, 279.1, 261, 275; 425/110, 125, 173, 444, 171; 269/7; 83/915.5; 427/4, 289; 350/507, 518, 521, 523

[56] References Cited

U.S. PATENT DOCUMENTS 1,353,477  9/1920  Jamieson .................. 425/444 X
4,210,384  7/1980  Meyer et al. .............. 350/523 X
4,248,821  2/1981  Van Dellen ............... 264/135

Primary Examiner—Jan Silbaugh
Assistant Examiner—Leo B. Tentoni
Attorney, Agent, or Firm—Gary, Juettner & Pyle

[57] ABSTRACT

A method and apparatus are disclosed for quickly and exactly locating a desired structure in a specimen or the like located on a plate or slide, and then preparing an accurate, embedded specimen block for later use, and particularly for preparing thin sections, e.g., 0.1 microns or less, on a microtome machine, for microscopic examination.

17 Claims, 7 Drawing Figures

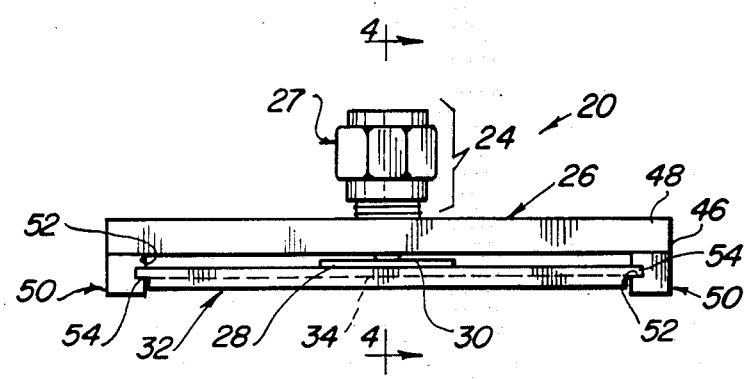
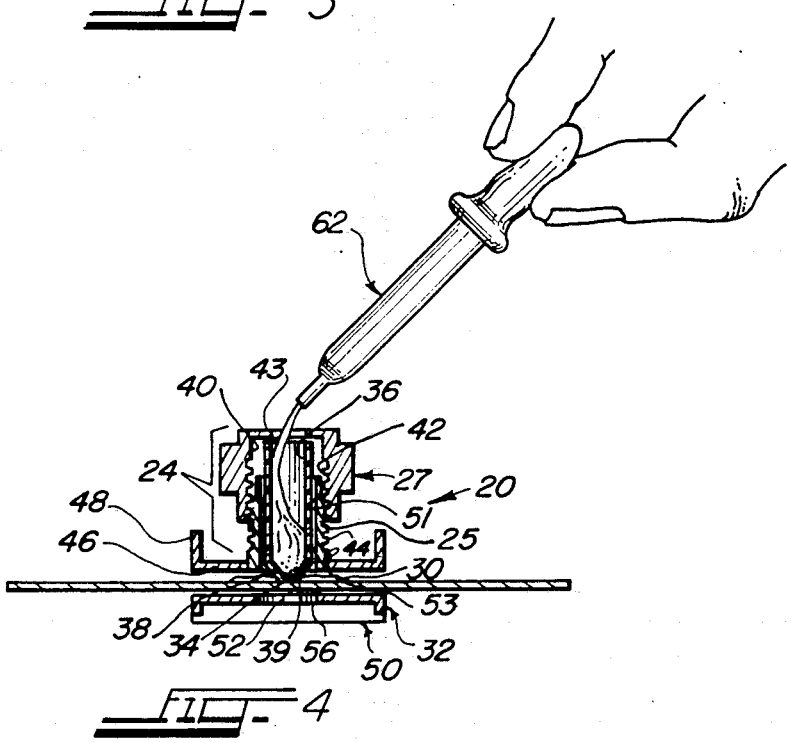
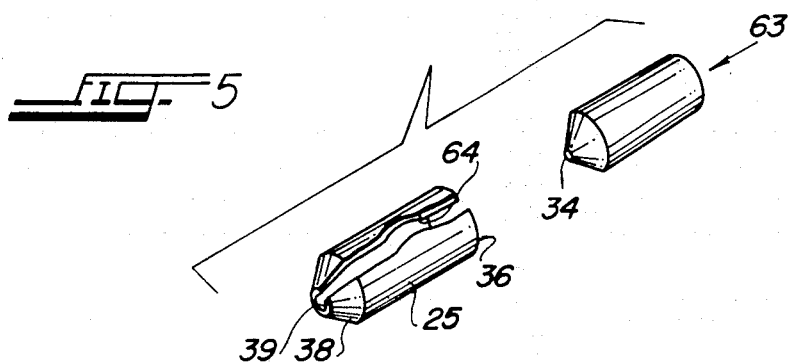

METHOD AND APPARATUS FOR LOCATING AND EMBEDDING A SPECIMEN

This invention relates to a method and apparatus for quickly locating a desired tissue structure or the like in a specimen, such as one mounted on a microscopic slide, and accurately preparing an embedded (or reembedded) specimen block for subsequent sectioning, and particularly for the preparation of such embedded specimen block for making thin sections on a microtome machine or the like, for further examination under an electron microscope.

This application also relates to a corresponding application Ser. No. 729,950, entitled "Capsule And Clamping Apparatus For Locating And Embedding A Specimen And A Method For Using The Same", and filed on May 2, 1985, issued as U.S. Pat. No. 4,595,549 on June 17, 1986 to Dr. Tohru Inouye and Lai-Chun Jannie Tong, and now assigned to Syprocode Inc., an Illinois corporation. The cross-referenced application is particularly directed to a method and apparatus for preparing thicker sections.

BRIEF DESCRIPTION OF THE PRIOR ART

By way of background, usually when preparing for electron microscopic examination, a preliminary examination of a conventional slide specimen is first made with a lower power microscope to locate, for example, a particular tissue structure of interest, such as a cell. The desired structure may be visibly very small; for example, a cell may have a visible length and width on the order of 20 microns or less. In order to examine at high magnification, for example, the cell's interior, what is done is first to cut a thick section, 1 to 6 microns, off the original specimen to expose its structure. This thick section is then examined at still higher power for again the desired structure. After the desired tissue structure is located, a special specimen block is prepared from this thick section for sectioning into thin sections 0.08 to 0.10 microns thick. As the thick section is extremely small to start with, it is very difficult to make a proper specimen for cutting the even smaller thin sections using the following prior art techniques.

According to the prior art, one method for preparing such sectioning specimen block was to use a conventional capsule such as sold by Better Equipment for Electron Microscope Company of Bronx, New York under the trademark BEEM. This capsule is of the type to fit the specimen holder of a microtome machine (such as of the general type shown in U.S. Pat. No. 4,484,503 and/or U.S. Pat. No. 3,845,659 or sold under the respective trademarks and manufactured by the following:

SORVALL ULTRAMICROTOME
DuPont Instrument Products
Newton, Conn.,

REICHERT OmU2
C. Reichert Optische Werke, A.G.
Wien, Austria, and

ULTROTOME III
LKB
Bromma, Sweden),

As shown in FIG. 1, a small part of the pointed end of the capsule was manually off, and then the technician tried to manually locate this cut opened end over the desired tissue structure. Problems arose as it was impossible to manually cut off the end of the capsule perfectly perpendicular to its axis. Other technicians tried to hold the capsule in place manually. The capsule was then filled with an embedding material, such as a suitable epoxy resin. The resin eventually hardened to form a block conforming to the shape of the capsule, hopefully, with the desired tissue specimen on its tip. The hardened block was then mounted in the microtome machine and sectioned. All too many times the resulting epoxied embedded specimen was inexact as the capsule had been held at even a slight angle while initially positioned or the resin hardened. Thus, after the resin hardened, it was difficult if not impossible to accurately and exactly cut the embedded tissue as it too was at an angle, instead of being perpendicular, to the relative path of the cutting edge of the blade of the microtome machine. If the capsule and resulting embedded epoxy resin held tissue specimen was off even slightly from perpendicular, a few seconds of a degree or less, it made accurate sectioning of the specimen difficult, if not impossible. Generally in order to make an accurate sectioning cut of say 0.08 to 0.10 microns thick from a 1 to 6 microns thick material over a surface (500–1000 microns wide and long), the path of the cutting edge of the microtome blade relative the specimen being sectioned had to be in angular alignment within a fraction of a second (1/6 of a second or less generally being acceptable). That is, it is extremely important to get the face of the resin block containing the specimen, to align parallel to the relative path of the cutting edge of the blade of the microtome machine. Of course, when the initial angular alignment of the tissue specimen in its resin block was even a few seconds off perpendicular, it made it all that more difficult, if not impossible, and time consuming to accurately align the block and/or specimen in the microtome machine to the required accuracy.

Another prior art technique used to form the specimen block was to invert the capsule on the slide so that its big end was in contact with the desired portion of the slide specimen. While with this approach the broad end of the capsule was utilized to hold it, perhaps, closer to perpendicular, it had the disadvantage of making it difficult, if not impossible, to locate the desired tissue accurately in the center, and then required the technician to trim the big end of the capsule and hardened epoxy to near a point, all without cutting off the desired target area.

Yet another prior art technique used was to leave the capsule's pointed end uncut or closed, and turned downwardly. Then the tissue to be embedded was dropped in the capsule, and the capsule filled with epoxy. Of course, with such technique the alignment of the tissue was totally random, and there was literally no way to insure the desired structure would appear at the face of the hardened block oriented in the proper manner.

While these prior art techniques were to some degree suitable for lower power microscopic examinations as the requirements are less critical, when it came to high power microscopic examinations, such as with an electron microscope, they were totally inadequate. No matter which prior art technique was used, all too frequently because the desired tissue was not properly located, or located at even a very small angle, the cut section was not correct or exact enough for further study. For example, the microtome cut would not be deep enough, leaving the tissue's structure unexposed, or too deep so that the desired tissue structure was cut away and/or destroyed. In the past, many, many tries were needed to obtain just the exact section desired for further examination.

The inaccuracies made it extremely difficult for even a well trained, experienced technician to estimate where and how much of the cell specimen to cut off with the microtome machine. If the particular tissue under investigation was destroyed while making the cut on the specimen, it then becomes necessary to start all over again by going back to the slide specimen to try to locate another suitable area, if such can be found, and begin all over. Heretofore, much valuable time and effort had been lost in trying to prepare such specimens.

BRIEF DESCRIPTION OF THE INVENTION

The present invention provides a method and apparatus by which, after a little training and experience, a technician can quickly prepare a correct thin (0.10 to 0.08 microns) sectioning specimen for high power microscopic examination, such as with an electron microscope, generally on the first try. The method of the present invention comprises the steps of accurately locating the subject tissue (which may itself be only 6 to 1 microns thick) on a slide, such as a conventional microscopic slide or other suitable flat, glass, plastic, etc. surface or the like, maintaining a capsule which is to contain the embedding epoxy resin, or other suitable material forming the specimen block, at a known fixed angle, preferably generally perpendicular, to the slide, and then embedding the desired tissue specimen in epoxy resin, or other suitable material, and permitting the same to harden while still holding the capsule in the perpendicular position. The apparatus for carrying out the method comprises a slide locating means for positioning the apparatus relative to a slide carrying the specimen and capsule holding means for holding the capsule for forming the embedded specimen, perpendicular to the slide. The slide locating means is constructed and sized so that it can be located over any desired part of the slide. In the preferred form the locating means comprises a base plate for receiving the slide and an upper portion connecting to the base plate on which capsule holding means is located.

It is pointed out that while it is desirable that the angle be exactly perpendicular, because of the fixed nature and repeatability, the method and apparatus can tolerate slight deviations in the angle and yet give good results. This is because with the present invention any variation is still considerably less when compared to the prior art techniques, which were much more random and divergent.

By practicing the method and using apparatus of the present invention, specimens are quickly and easily prepared for sectioning. The desired tissue structure can be quickly located on the slide by viewing through a conventional microscope, if need be. The capsule can be accurately located exactly over the desired target area, and the latter can be embedded very close to, if not exactly, perpendicular to the axis of the capsule so that it then becomes relatively easy for a trained technician to make minor adjustments in alignment and to estimate the desired depth of cut to make on the microtome machine, such as one of those described above, to section through the tissue at the desired location.

It is a primary object of the method and apparatus of the present invention to permit a technician to quickly prepare specimens for embedding.

Another object of the method and apparatus of the present invention is to provide for the accurate location of an embedding capsule on a slide specimen.

A further object of the method and apparatus of the present invention is to provide accurate embedding of a specimen to be further processed, as by sectioning with a microtome machine or the like.

Still another object of the present invention is to provide for fast and efficient preparation of a specimen for further study by sectioning and viewing under an electron microscope.

BRIEF DESCRIPTION OF THE PREFERRED EMBODIMENT

FIG. 3 is an elevational view of the apparatus of the present invention assembled on the microscope slide.

FIG. 4 is a cross-sectional view taken on the lines 4—4 of FIG. 3.

FIG. 5 is a perspective view showing the embedded specimen mounted on the resin block and separated from the capsule in which it was formed.

DESCRIPTION OF THE PREFERRED INVENTION

Figure 1:
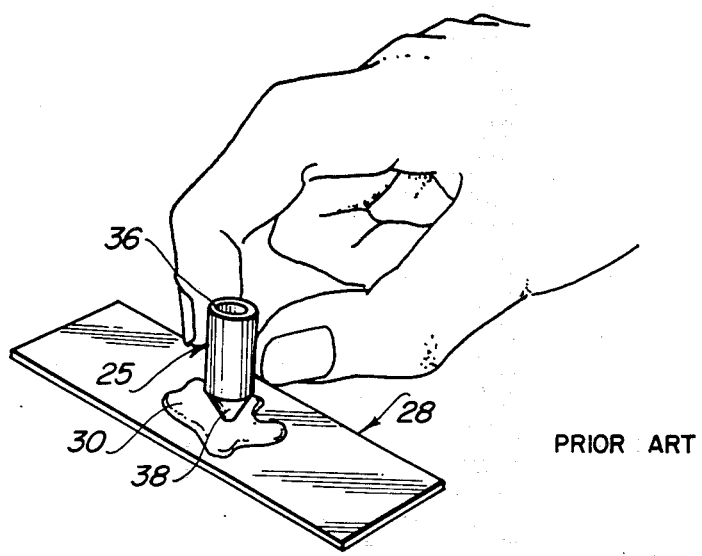
FIG. 1 is a perspective view showing one of the prior art approaches.
Figure 2:
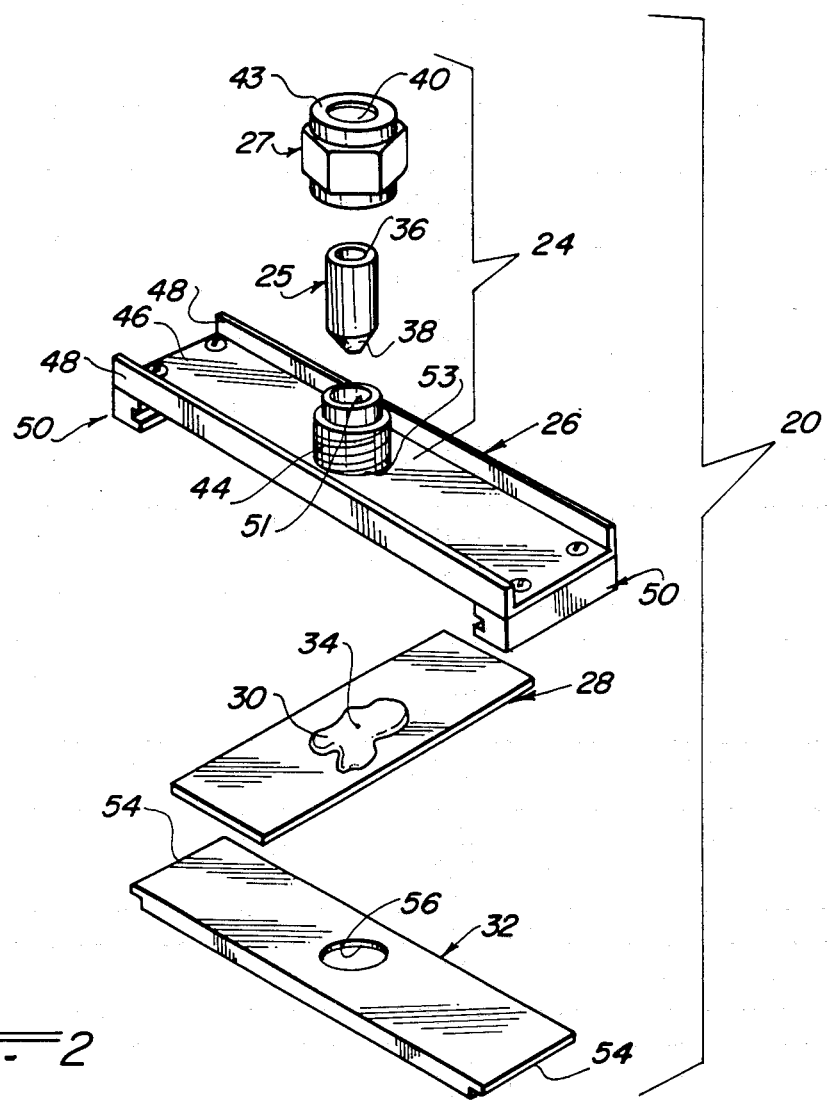
FIG. 2 is an exploded perspective view of one embodiment of apparatus for carrying out the method of the present invention for making a small embedded specimen, suitable for later sectioning, from a microscope slide carrying a larger specimen.

Referring to FIG. 2, the apparatus 20 of the present invention is illustrated and comprises, capsule holding means 24 for, in this instance, a cylindrical style capsule 25. The capsule holding means 24 includes a cap 27. Apparatus 20 further comprises locating structure 26 to which the capsule holding means 24 is attached and a base plate 32. All these parts cooperate with a conventional microscope slide 28 which carries a large slide specimen 30 thereon. The latter, in turn, includes the extremely small portion 34 containing, for example, a single cell or a specific structure which is to be sectioned and subject to further investigation under an electron microscope.

The embedding capsule 25 is generally similar to the conventional capsules heretofore used for such purpose with a microtome machine, except that its closure lid structure (not shown), which can cover the large open end 36 of the capsule, has been removed, and any closure lid attaching tab (not shown) has also been removed. A capsule, such as sold by Better Equipment for Electron Microscope Company of Bronx, N.Y. under the name BEEM Capsule, may be suitably modified for use with the present invention. As is noted, the small end 38 of the capsule has been cut away as with a lathe or other exact, accurate cutting device to form a perpendicular, small embedding opening 39 which may be centered over the small specimen 34 to be embedded, sectioned, and further studied. While the BEEM capsule can be used, it may be preferable to use the capsule described in the above mentioned corresponding application Ser. No. 729,950, as desired accurate opening (39) at the bottom is already preformed.

The cap 27 is essentially a standard ½—20 NC thread commercial brass cap sold at any hardware store and has an interior opening 40 with a female threaded portion 42 (FIG. 4) and an upper flange 43. The cap 27 cooperates in the manner illustrated in FIG. 4 with a male threaded member or portion 44 on the locator structure 26 to move and retain the capsule in the capsule holding means 24.

The remainder of the locator structure 26 comprises an elongated planar member 46, in this instance formed from an available channel member having raised flanges 48 at its long sides. Normally the planar member 46 selected would have sufficient strength of its own that the flanges could be eliminated. The previously mentioned male threaded member 44 has a central opening 51 sized to relatively snugly accept the capsule 25 and is located generally centrally of the planar member 46 and secured thereto. The opening 51 is formed perpendicular to the slide 28 so that the capsule 25 held therein will move in a perpendicular direction to the slide. Generally, an opening drilled with a good drill press will be sufficiently perpendicular. The planar member 46, likewise, has an opening 53 (FIG. 4) therein, which is aligned with opening 51 and receives the lower end of member 44. Alternatively, the capsule holding means 24 and locator structure 26 could have been made integral.

Each end of the planar member 46 is fitted with legs 50 having slots 52 formed on their inside surfaces for receiving and holding the base plate 32. The slots 52 are spaced a sufficient distance below and parallel to the bottom of the planar member 46 to easily permit a slide to pass, generally about 0.2 centimeter being sufficient. As is shown in FIG. 2, the legs are held to the channel formed planar member 46 as by, in this instance, screws. Of course, other fasteners could be used, or the legs could be made integral with the member 46.

The base plate 32 is elongated and of a length so that its opposite, shorter edges 54 fit snugly into the slots 52 and hold the base plate 32 in place parallel to the planar member 46. As is shown, portions of the base plate 32 beneath the edges 54 are cut away to accommodate the legs. Of course, the slots 52 could have been made the full thickness of the base plate and the base plate ends left their full thickness. As is shown, to assist in aligning the specimen 34 to be sectioned with the small opening 39 in the capsule, the portion of the base plate 32 that is alignable with the capsule holding means 24 is provided with a viewing opening 56.

The locator 26 and base plate 32 are of a length to permit any portion of a conventional microscope slide 28 to be located beneath the opening 51 in the capsule holding means 24. The widths of these two parts (26 and 32) are sufficiently large to stably support the slide.

The apparatus of the present invention may be used in the following manner. As is shown in FIGS. 3 and 4, the slide 28 with the small specimen 34 within the larger specimen 30, is approximately located over the viewing opening 56. If need be, any markings made on the back side of slide 28 may be checked for rough alignment through the viewing opening 56. The base plate 32 is then slipped fully into the slots 52 in the legs 50, thus automatically approximately aligning the capsule holding means 24 with the small specimen 34. The capsule 25 may then be partially pressed into the opening 51.

Then the slide 28 can be maneuvered with respect to the opening 51 until the small specimen 34 is located exactly beneath the small opening 39 cut in the capsule's pointed end 38. The marking made earlier on the bottom of the slide 28, which is viewable through opening 56, may be sufficient to obtain such relationship, but if need be, the entire apparatus 20, (with capsule 25), including slide 28 could be mounted on a microscope and the desired final alignment achieved. When the desired final alignment is reached, the cap 27 is turned and screwed down so that the cap's flange 43 contacts the capsule 25 and moves it toward and into contact with the slide 28, thus holding the slide 28, capsule 25 and specimen 34 firmly in place in the opening 39. Of course, other type fastening means than the threaded cap and male threads 44 could be used to move the capsule into contact with the specimen. Alternatively, such structure could be dispensed with and the capsule merely pressed into contact with the glass slide by finger pressure, the fit between the opening 51 and capsule 25 being made sufficiently snug to retain the capsule.

As is shown, the resin is then placed into the big end 36 of the capsule 25 as with the dropper 62. After it hardens in the capsule 25, the formed epoxy resin block 63 (FIG. 5) therein with the small specimen 34 at its tip may be removed from the apparatus 20 manually. The specimen 34 is firmly affixed in the resin and easily removed from contact with the glass slide without damage.

Thereafter, the side of the capsule 25 can be longitudinally slit or cut away, as illustrated at 64 in FIG. 5. The specimen 34 on the resin block 63 may then be mounted in the microtome machine and cut away or sectioned as desired. As the specimen 34 and the face of the resin block are very nearly, if not exactly, parallel to the path of the cutting edge of the microtome blade, the sections can be easily cut. After sectioning, the sectioned portion may then be placed on a suitable, conventional grid (metal screen) specimen holder for the electron microscope and examined.

Figure 6:
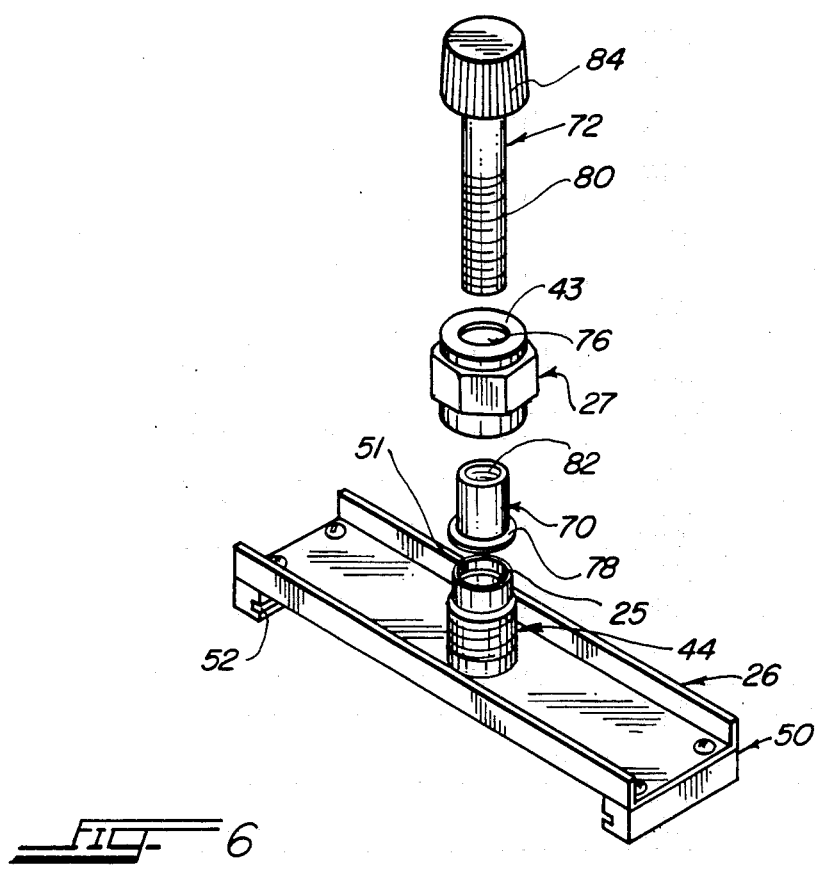
FIG. 6 is an exploded perspective view similar to FIG. 2, showing some of the apparatus of FIG. 2 with additional apparatus for removing the encapsulated specimen.
Figure 7:
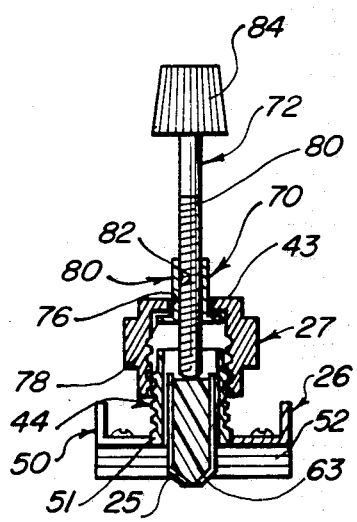
FIG. 7 is a cross-sectional view taken through the apparatus shown in FIG. 6 after its assembly.

While the hardened resin filled capsule 25 can be manually removed from the opening 51 in the member 44, at times that may be difficult. To make this task easier, additional ejection apparatus is illustrated in FIGS. 6 and 7 and comprises a threaded bushing 70 and a ejection rod 72. These parts cooperate with the cap 27 to eject the hardened resin filled capsule from the threaded member 44. As is shown, the cap 27 is removed and bushing 70, which is sized to fit within the top opening 76 in the cap 27, is inserted therein. The lower flange 78 on the bushing 70 engages with the underside of the flange 43 of the cap 27. The cap 27 may then be screwed back in place on the threaded member 44. Then the ejection rod 72, which has a male threaded end 80, is screwed into the female threaded opening 82 in the bushing 70. The capped end 84 of the ejection rod 72 forms a knob to assist in turning the ejection rod. As the ejection rod is screwed in, it engages the hardened resin filled capsule 25 (and block 63) and drives it from the opening 51. The length of the threaded portions of the bushing 70 and ejection rod 72 are of sufficient length to substantially fully drive the capsule from the opening 51. Of course, it may be preferable to make the bushing 70 an integral part of or fuse or otherwise secure it to the cap 27.

While the present invention was described in connection with a tissue specimen, it should be understood that the method and apparatus could also be used with other specimens, such as ones prepared from tissue cultures or any specimens, biological or otherwise, that needs to be viewed or studied in thin sections. As used herein the specimens on the slide are defined to include all such specimens. Also, while the apparatus and method of the present invention were described with one type capsule and block, it should be understood that the apparatus and method could be utilized with other size or type capsules and blocks for making embedded specimens. For example, the capsule and blocks could be rectangular, instead of cylindrical, or just tips to be secured to other elements, the resulting blocks then being secured in the collet, chuck or vise of the microtome. While the present invention is particularly useful in preparing thin section specimens, it can also be used to prepare thick section specimens.

While only one embodiment of apparatus and method of the present invention has been illustrated and described, from the foregoing, it should be understood that variations, modifications, and equivalent structures and steps thereof fall within the scope of the appended claims.

What is claimed is:

1. A method for forming an embedded specimen suitable for sectioning with a microtome machine or the like in a capsule having open, opposite specimen and pouring ends, from a slide mounted specimen or the like, comprising the steps of:
   A. locating the desired to be embedded specimen on the slide specimen,
   B. mechanically holding the embedded capsule adjacent the slide in substantially perpendicular relationship to the slide,
   C. viewing the specimen from the side of the slide opposite the capsule,
   D. aligning the to be embedded specimen with the open specimen end of the capsule,
   E. moving the capsule relatively toward the slide to hold the open specimen end of the capsule in substantially sealed contact with the specimen on the slide,
   F. positioning the slide and capsule with the open pouring end of the capsule above the specimen end and the slide, and
   G. pouring embedding material into the open pouring end of the capsule and permitting the embedding material to flow downwardly toward the specimen end and harden about the to be embedded specimen while the capsule is still being held mechanically substantially perpendicular to the slide.

2. A method as in claim 1, wherein in step E the capsule is relatively moved substantially perpendicularly toward the slide.

3. Apparatus for forming an embedded specimen for sectioning with a microtome machine or he like, with a capsule having opposite, open specimen and pouring ends and a slide mounted specimen or the like, comprising capsule holding means for holding said capule in which the embedded sepcimen is to be embedded, locator means for locating said capsule holding means at a spaced distance from the slide mounted specimen, a base plate for holding the slide substantially perpendicular to said capsule holding means, said capsule holding means permitting relative movement of the capsule into sealed contact with the slide specimen and removal of the capsule from the capsule holding means, said locator means and base plate having cooperating portions for holding the two together so that the slide closely adjacent said capsule holding means is well supported, said capsule holding means being open adjacent the pouring end of the capsule so that light may enter the capsule, said base plate having a viewing opening aligned with said capsule holding means for ascertaining the alignment of the to be embedded specimen and the specimen end of the capsule, said apparatus being positionable to locate the capsule holding means above said base plate so that embedding material can be poured through said open capsule holding means, into the open pouring end of hte capsule and into the capsule, whereby accurate embedded specimens can be quickly formed.

4. Apparatus as in claim 3, wherein said locating means and base plate are sized to permit any portion of the slide to be aligned with said capsule holding means.

5. Apparatus as in claim 4, further comprising one or more legs on one of said locating means and base plate and means for holding said base plate in position beneath said capsule holding means.

6. Apparatus as in claim 5, wherein said one or more legs are located on said locator means, said legs having cooperating means to receive said base plate.

7. Apparatus as in claim 3, wherein said capsule holding means has an opening therein, extending away from said locator means, adapted to be aligned, substantially perpendicular to the slide, and to snugly receive he embedding capsule.

8. Apparatus as in claim 7, wherein said capsule holding means includes means for moving the capsule relative to said opening and at least into contact with the slide specimen.

9. Apparatus as in claim 8, wherein said moving means comprises a cap member and cooperating fastening means on said cap member and capsule holding means for drawing said cap and the capsule relatively toward the slide.

10. Apparatus as in claim 9, wherein said fastening means comprises threaded portions on said cap and cooperating threaded portion on said capsule holding means.

11. Apparatus as in claim 7, further comprising ejection means for ejecting the capsule containing the embedded specimen from said capsule holding means.

12. Apparatus as in claim 11, wherein said ejection means comprises an ejection rod cooperating with a portion of the remainder of the apparatus to eject the capsule.

13. Apparatus as in claim 12, further comprising a threaded bushing adjacent said cap member, and said ejection rod is threaded and cooperates with said threaded bushing to move the capsule out of said capsule holding means.

14. Apparatus as in claim 8, wherein said moving means can move the capsule completely through said capsule holding means.

15. Apparatus for forming an embedded specimen for sectioning under one micron thick sections with a microtome machine or the like with an embedding capsule having opposite, open specimen and pouring ends and a slide specimen or the like, comprising capsule holding means for holding said embedding capsule substantially perpendicular to the slide, locator means for locating said capsule holding means at a spaced distance from the slide mounted specimen, a base plate for holding the slide specimen substantially perpendicular to said capsule holding means, said base plate having a flat portion for supporting the slide specimen closely adjacent said capsule holding means, said locator means and base plate being sized to permit any portion of the slide to be located in alignment with said capsule holding means, a pair of legs on oppose ends of said locator means, said legs and base plate having cooperating means to hold said base plate in position beneath said capsule holding means, said capsule holding means having a capsule opening open at both ends thereof and adapted to be aligned substantially perpendicular to the slide and to receive the embedding capsule, said base plate having a viewing opening therein aligned with said capsule opening in said capsule holding means, said capsule holding means including means for moving the capsule through said capsule opening therein and into sealing contact with the slide in the form of a cap member and fastening means for drawing said cap relatively toward the slide.

16. Apparatus as in claim 15, wherein said locator means and base plate are, planar and said legs are located at the ends of said locator means, said legs having slots therein for receiving said base plate, said base plate having a viewing opening therein capable of being aligned with said capsule opening in said capsule holding means.

17. Apparatus as in claim 16, wherein said fastener means comprises cooperating threaded portions on said capsule holding means and said cap for moving the capsule toward the slide, and further comprising an ejection means for driving the capsule from said capsule opening.

* * * * *